(12) United States Patent
Ramos De La Fuente

(10) Patent No.: US 7,399,343 B2
(45) Date of Patent: Jul. 15, 2008

(54) SYSTEM AND DEVICE FOR MASS TRANSFER AND ELIMINATION OF CONTAMINANTS

(76) Inventor: Ruben Ramos De La Fuente, Morelos No. 163 Col. El Carmen, Coyoacan (MX) 03810

( * ) Notice: Subject to any disclaimer, the term of this patent is extended or adjusted under 35 U.S.C. 154(b) by 537 days.

(21) Appl. No.: 10/528,683

(22) PCT Filed: Sep. 20, 2002

(86) PCT No.: PCT/MX02/00091

§ 371 (c)(1),
(2), (4) Date: Mar. 21, 2005

(87) PCT Pub. No.: WO2004/026440

PCT Pub. Date: Apr. 1, 2004

(65) Prior Publication Data

US 2006/0011062 A1  Jan. 19, 2006

(51) Int. Cl.
*B01D 47/16* (2006.01)
(52) U.S. Cl. .............................. 95/215; 96/286; 96/287; 96/289
(58) Field of Classification Search .................. 95/215, 95/218; 96/281, 283, 286–289; 261/83, 261/91–92
See application file for complete search history.

(56) References Cited

U.S. PATENT DOCUMENTS

| | | | | |
|---|---|---|---|---|
| 17,448 A * | 6/1857 | Partz | ............................. | 159/10 |
| 862,646 A * | 8/1907 | Little | ............................. | 96/289 |
| 1,409,593 A * | 3/1922 | Schram | ............................. | 96/228 |
| 1,778,571 A * | 10/1930 | Stratton | ............................. | 261/83 |
| 1,846,057 A * | 2/1932 | Ilg | ............................. | 96/287 |
| 1,942,085 A * | 1/1934 | Carey | ............................. | 96/289 |
| 2,703,228 A * | 3/1955 | Fleisher | ............................. | 96/235 |
| 3,350,877 A * | 11/1967 | Bowman | ............................. | 60/310 |
| 3,353,337 A * | 11/1967 | Gale | ............................. | 96/262 |
| 3,544,084 A * | 12/1970 | Macrow | ............................. | 261/29 |
| 3,711,071 A * | 1/1973 | Urbanowicz | ............................. | 261/92 |
| 2005/0087071 A1 * | 4/2005 | Petz et al. | ............................. | 96/52 |

* cited by examiner

*Primary Examiner*—Duane Smith
*Assistant Examiner*—Ives Wu
(74) *Attorney, Agent, or Firm*—Peter J. Rashid

(57) ABSTRACT

A system and a device that are used for liquid-gas phase mass transfer with elimination of contaminants. The systems includes a plurality of liquid membrane-producing cells. Upon contact, the liquid membranes collapse with a gas stream and the collapsed liquid material covers the suspended particles, and eliminates them by decantation. Moreover, the membrane cells increase the speed of the gas stream and cause the gas stream to hit the surface of the liquid at an incident angle of 45°, which serves to improve the transfer of vapor into the gas.

14 Claims, 4 Drawing Sheets

US 7,399,343 B2

SYSTEM AND DEVICE FOR MASS TRANSFER AND ELIMINATION OF CONTAMINANTS

This invention refers to a system and apparatus for transferring vapor molecules from a liquid stream to a gas stream. Particularly, it refers to an air humidification and pollutants filtrating system and the corresponding apparatus. More specifically, a system and an apparatus to filter, humidify, or mix air through collapsible liquid aqueous membranes are described.

This invention will be described in relation to air humidifiers where liquid molecules (water) are transferred by a mass-transfer phenomenon to a gas stream (air) in contact with the liquid.

BACKGROUND OF THE INVENTION

Atmospheric air is a mixture of dried air, and steam water and is called humid air. This mixture of gases is the one that is conditioned in ambient control systems by means of humidifiers, and conditioned air units. From now on, the word "air" will be used to denote the mixture of dried air, and water vapor as naturally occurring in the atmosphere.

According to standard 55-1981 from ANSI/ASHRAE (American National Institute of Standards/American Society of Heating, Refrigeration and Air Conditioning Engineers) a series of ideal conditions for comfortable indoor environments were set forth. According to this standard, humidity is a determinant factor for human comfort. At temperatures between 20° C. and 26° C. an indoor environment is comfortable as long as the air humidity is between 30 and 70%.

From the above, there is a need for humidifiers as co-adjuvants of human comfort.

In the state of the art, a diverse kind of humidifiers is known; humidifiers are classified according to their functions. Such classification consists of:

Evaporative humidifiers: In such systems, a fan makes air circulate through a moisturized material. Water contained in the material is transferred to the air stream, thereby increasing the relative humidity of the air stream.

Liquids have a physicochemical property called vapor pressure. Such property determines the balance between the vapor phase, and the liquid phase of a liquid. By virtue of such property, a liquid will always tend to establish a balance between the liquid and vapor phases.

The evaporation phenomenon takes place when vapor is generated as a result of the balance between the liquid-vapor phases. If a gas stream absorbs vapor at balance with the liquid phase, fresh vapor will be generated to re-establish the liquid-vapor balance.

In the evaporative humidifiers, an air stream takes up the vapor that is balanced with the liquid phase, the balance is broken, and new vapor is generated to re-establish the balance. The air that comes out of the humidifier is humid air.

The evaporative humidifiers have the disadvantage that the moisturized material can become a source for the growth of fungus, algae, and aerobic germs.

U.S. Pat. No. 4,844,842 published on the 4$^{th}$ of Jul., 1989 describes an apparatus of this sort. According to such patent, the moisturizing element being formed as a rotatable disc. The bottom of the disc is submerged in a water bath or in an aqueous liquid while the top is in contact with an air stream. When such disc rotates, the top is submerged in the liquid while the submerged part emerges already wet, and gets in contact with the air stream.

U.S. Pat. No. 5,945,038 describes an evaporative humidifier that consists of an absorbent material where a portion of the humidification material is submerged, and the upper portion is exposed to air, in such patent the use of a floater to control the water supply is also described.

Boiling Humidifiers. In such evaporators, an air stream is mixed with a steam stream that was obtained from boiling water.

Such evaporators have the advantage of eliminating all kinds of microorganisms; however, they generate a "white dust" that consists of insoluble salts and minerals contained in water that are entrained along with the steam streams. On the other hand, boiling humidifiers have the disadvantage of using a great deal of energy to boil water. On the other hand, such humidifiers do not provide the means to remove those pollutants already present in the air stream.

Warm Mist Humidifiers. These humidifiers operate with water vapor near the dew point temperature. Water vapor is cooled just before contacting the air stream, in such a way that a gaseous mixture of steam water and small droplets of water, and air is obtained.

Such units have the disadvantage of keeping air pollutants. Besides, such humidifiers do not provide means to remove pollutants present in the air stream either.

Cold Mist Humidifiers. In these humidifiers, water or an aqueous liquid is sprayed, and then mixed with the air. Such equipment has the disadvantage of keeping the pollutants, and microorganisms in the humid air stream.

Such humidifiers do not provide the means to remove those pollutants present in the air stream either.

Ultrasonic humidifiers. These humidifiers use high frequency vibrations to spray, and evaporate water.

The ultrasonic evaporators have the disadvantage of requiring very costly maintenance. Besides, these humidifiers do not provide the means to remove the pollutants present in the air stream either.

As above mentioned, the boiling humidifiers, the warm mist humidifiers, the cold mist humidifiers, and the ultrasonic humidifiers do not remove those pollutants present in the air streams so that in such humidifiers, the pollutants are entrained along with the humidified air stream.

On the other hand, in the case of evaporative vaporizers, still when the dust is removed by filtering the moisturized material, such dust that is in contact with the moisturized material promotes the growth of fungus, algae, and aerobic germs. Besides, as times passes by, the accumulated dust in the moisturized material tends to obstruct the air circulation through the moisturized material, and then affects water transfer to the steam stream.

To remove dust, different kinds of filters are known. Also, it is known the use of foam to control dust in mining environments, for instance, in carbon mines. The foam is generated by means of ejectors where an air stream is mixed with a water stream at high speeds.

U.S. Pat. Nos. 4,000,992, and 4,400,220 of Jan. 4$^{th}$, 1977, and Aug. 23$^{rd}$, 1983, describe a system for dust removal by bubbles into a cyclone.

Therefore, in the state of the art, there is no evaporator that also removes dust, and pollutants from the humidified air stream without generating fungus, algae, and aerobic germs.

For this reason, an object of the invention is to provide a system and an apparatus to transfer liquid molecules by evaporation to a gas stream in contact with the liquid.

For this reason, an object of the invention is to provide a humidifier system and an apparatus capable of eliminating air pollutants.

Another object of the invention is to provide a humidifier system, and an apparatus capable of eliminating dust and microorganisms from the air stream.

One more object of the invention is to provide a system of easy maintenance capable of efficiently humidifying, removing air particles, disinfecting, and providing aroma to the air.

DETAILED DESCRIPTION OF THE INVENTION

Figure 1A:
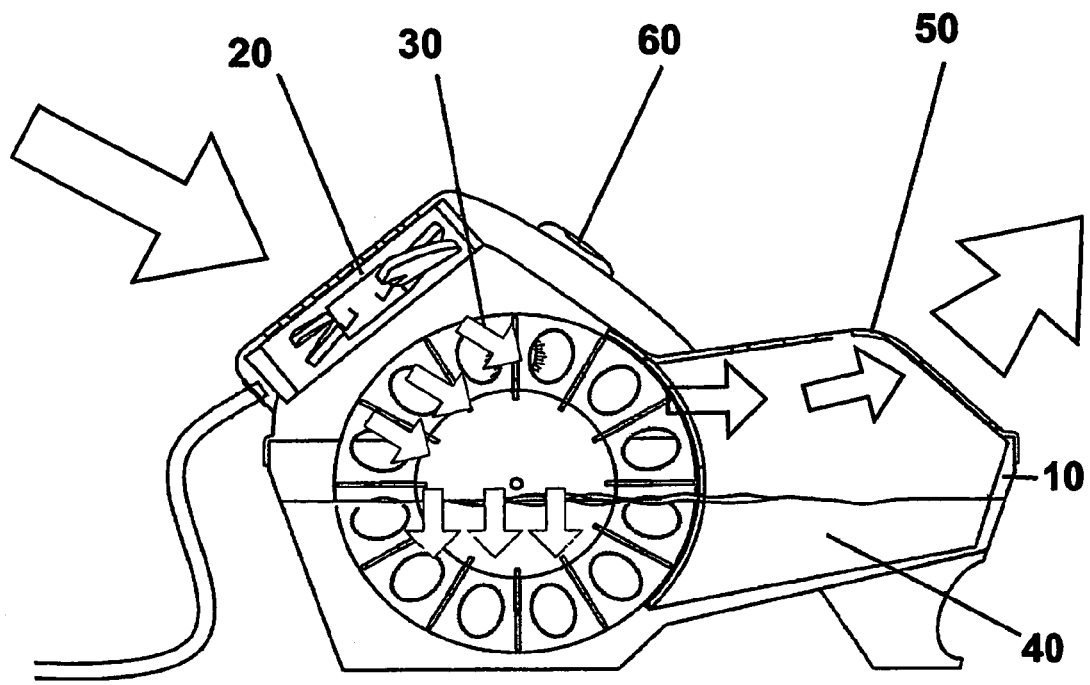
FIG. 1A shows the apparatus of this invention.

According to FIGS. 1A, 1B, 1C, and 1D, the humidifying apparatus of this invention consists of a housing 10 wherein the air convection means 20, the membrane generation means 30, the liquid supplying means 40, the ejection means 50, and the control means 60 are placed.

The housing 10 can be made of any material, for instance, metal, glass, wood, or plastic. In home applications, it is preferred to make the housing of plastic. Preferably, the housing material 10 should not chemically react with the gas or the liquid transferred to the gas stream.

The air convection means 20 comprises any means able to force the convection of air to be purified and humidified inside the humidifying apparatus. In FIGS. 1A, 1B, 1C, and 1D, such means is illustrated as an axial fan 21, however, any system that generates an air flow can be used, for example, piston, turbine, radial fan, blower, compressor, etc. Optionally, an external air stream can be used, for example a stream from a pipeline. The gas flow may be intermittent or continuous.

The air is forced to go through the membrane generation means 30.

Figure 1B:
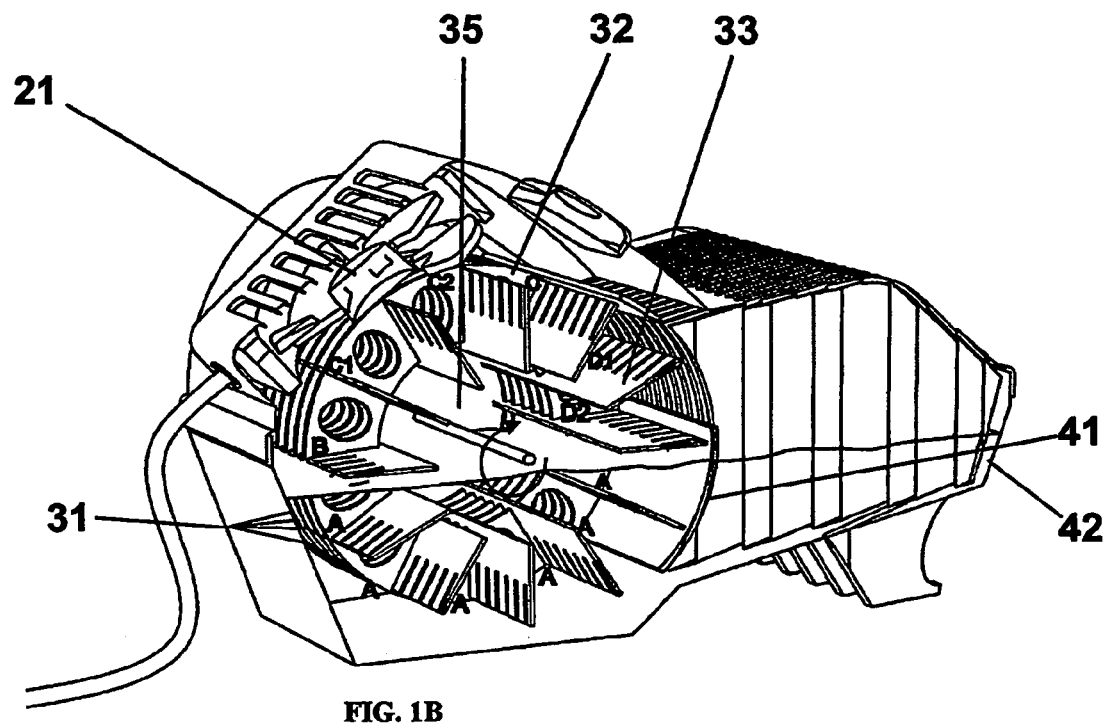
FIG. 1B shows the apparatus of this invention where the internal components of the apparatus are illustrated.
Figure 1C:
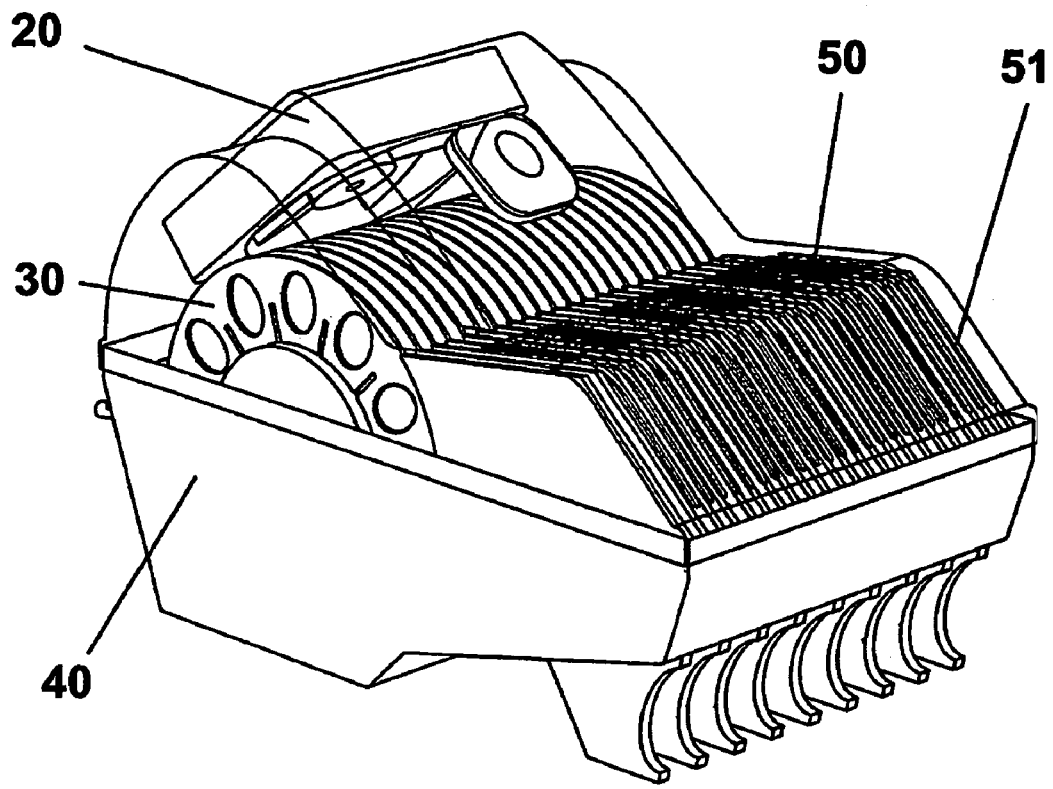
FIGS. 1C and 1D respectively show the front and rear components of the apparatus of this invention.
Figure 1D:
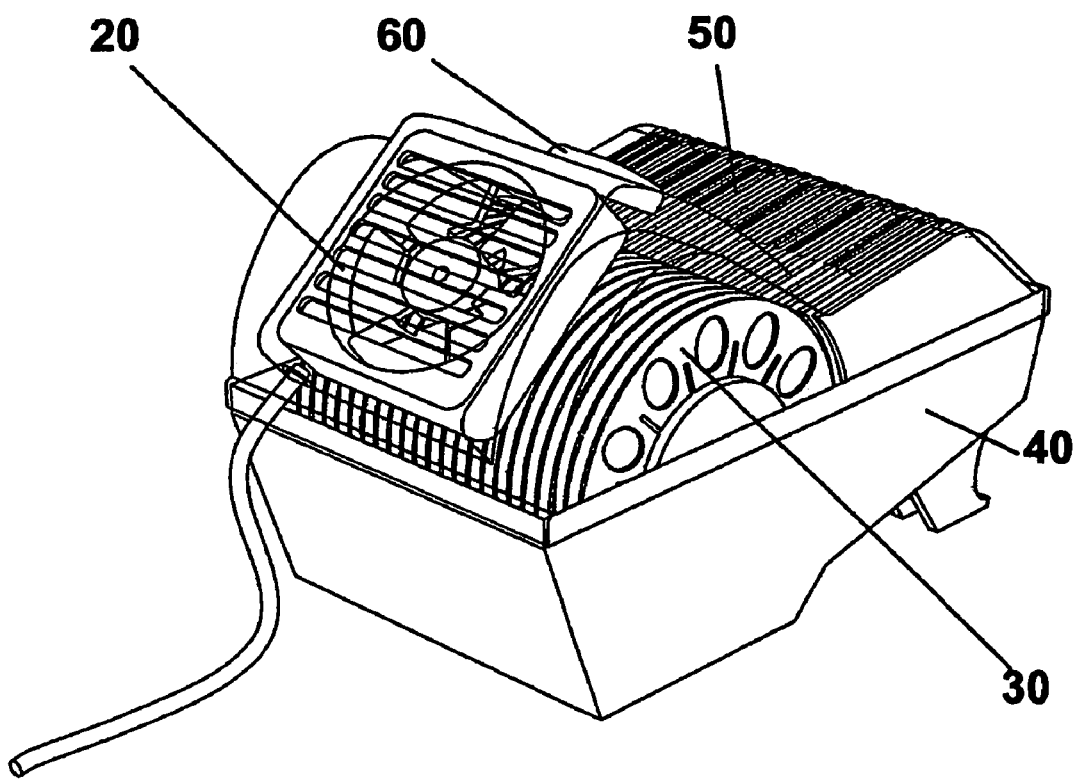
Figure 2:
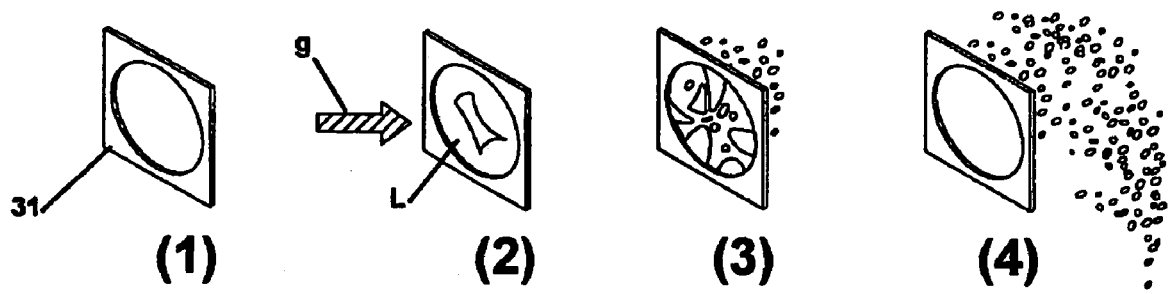
FIG. 2 shows the sequence of creation and collapse of the liquid membrane to remove solid particles and spray water according to this invention.
Figure 3:
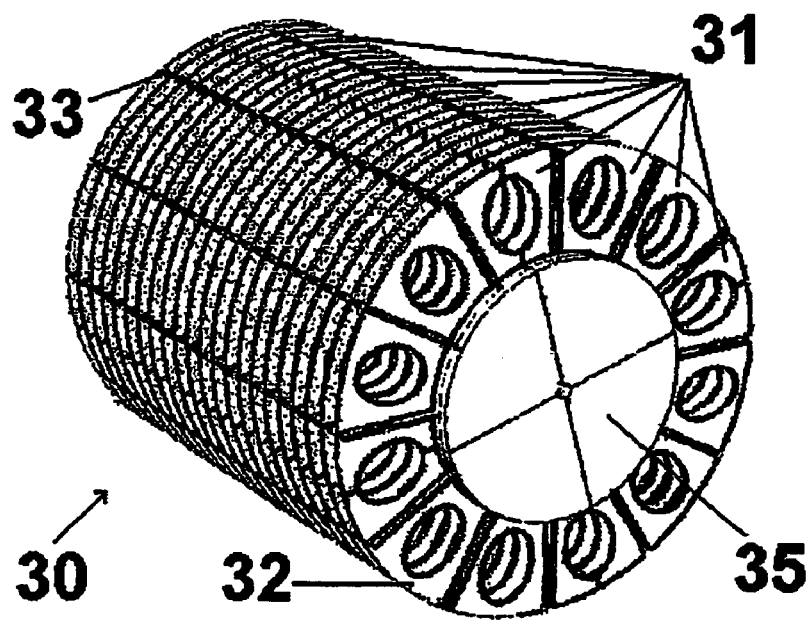
FIG. 3A shows the means to generate the membrane.
FIG. 3B illustrates a membrane cell.
Figure 3:
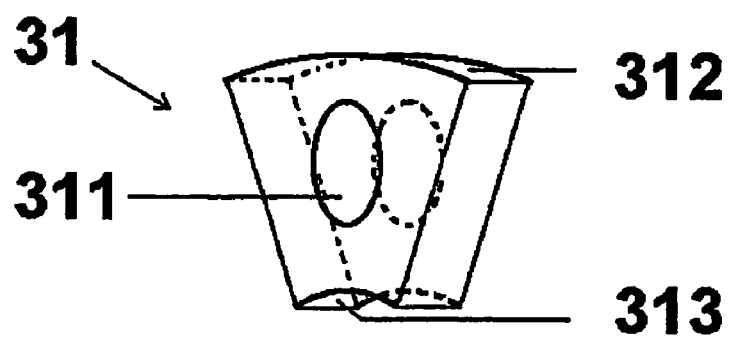
Figure 4:
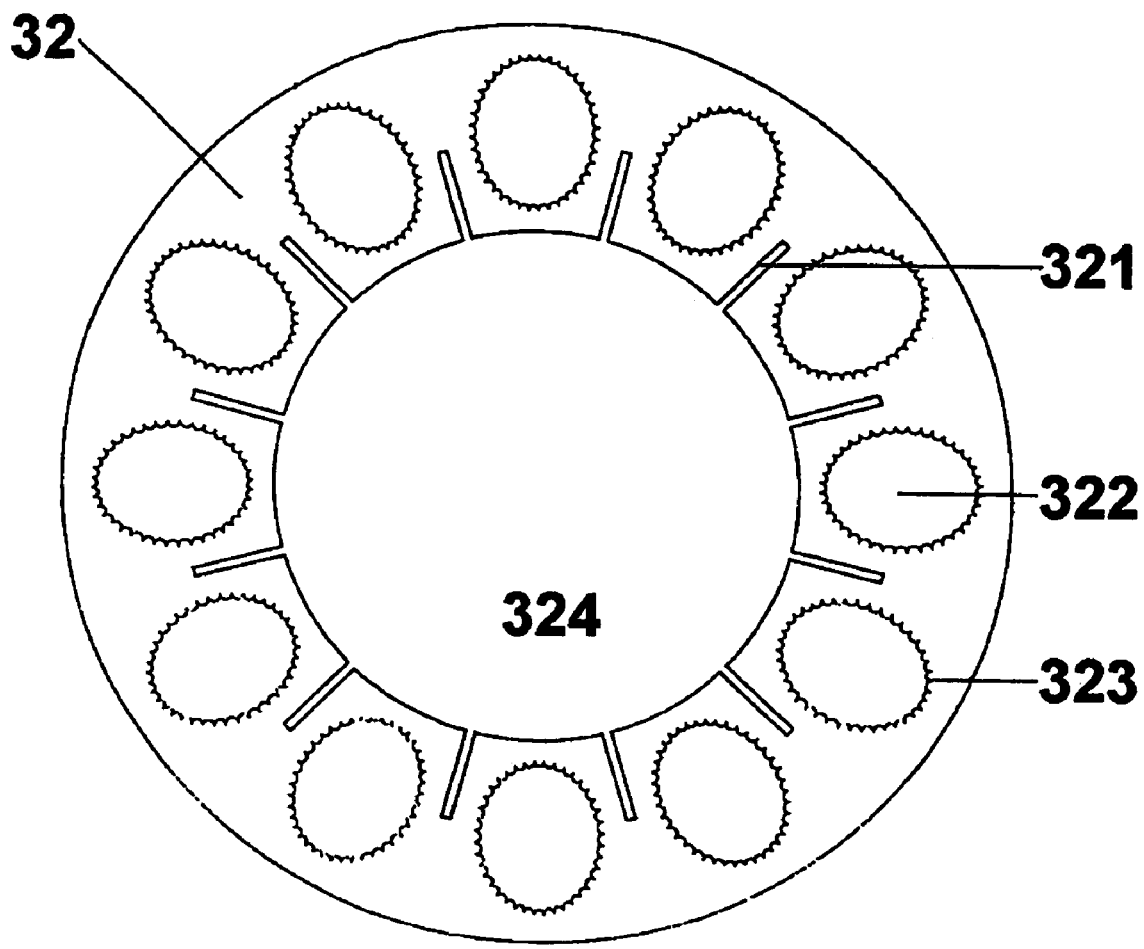
FIG. 4 shows a membrane disc.
Figure 5:
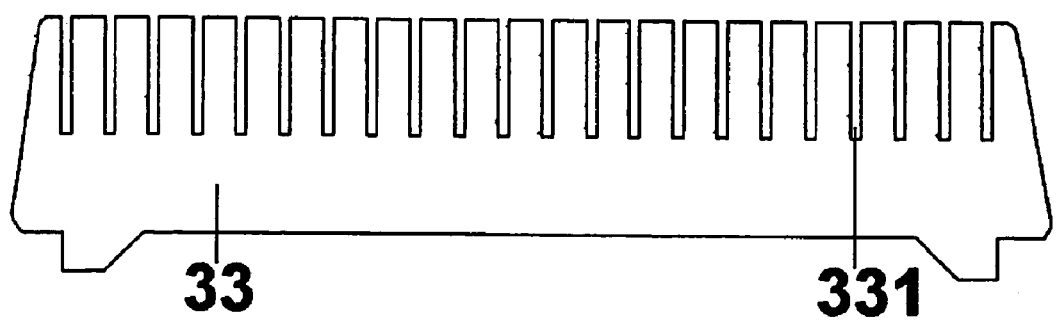
FIG. 5 shows an assembly plate of membrane discs.

The membrane generation means 30 consists of a plurality of membrane cells 31 that provides for surfaces to form aqueous membranes. The membrane generation means 30, and the membrane cells are illustrated in FIGS. 3A, and 3B, respectively.

The plurality of cells 31 is formed from a plurality of discs 32, and assembly plates 33. In FIG. 4, a disc 32 is shown, and in FIG. 5 an assembly plate 33 is illustrated.

The discs have a plurality of slots 321 and a plurality of orifices 322. The orifices 322 have a perimeter 323. The shape of the orifice and the shape of the perimeter of the orifice should be suitable to form a liquid membrane. As illustrated in FIG. 4, the orifices have an oval shape, and the perimeter of each oval has a wavy shape, in such a way to provide the largest contact surface favoring the formation of liquid membranes. Such arrangement has provided for the best results in membrane creation. Besides, such discs have a void center 324.

The assembly plate shown in FIG. 5 consists of a rectangular plate that has slots 331, such assembly plate 33 has a similar shape to that of a comb. The slots in the disc match with the slots 331 of the assembly plate to form the membrane generation means 30, which has a similar structure to that of a cylinder. In FIG. 1B, the assembly of plates 33 and discs 32 is illustrated.

As it will be readily apparent for an expert on the art, the discs can have a polygonal shape. The discs with a polygonal shape are considered included within the scope of this invention.

The center 324 of the discs 32 defines a chamber 35 inside the plurality of membrane cells 31 in a cylindrical arrangement.

The membrane cells 31 are formed in the spaces between the disc surfaces 32 and the combs 33. Such cells have the shape of an irregular cube that is widened in one of its faces. The cells 31 are illustrated in FIG. 3B. The plurality of discs 31 is manufactured of any suitable material to allow forming an aqueous membrane.

The membrane generation means 30 rotates continuously (or intermittently), so that the membrane cells 31 undergo the following operation stages:

(1) Liquid immersion;

(2) Membrane formation;

(3) Upcoming air and membrane breakage;

(4) Humid air ejection.

In FIG. 2, there is an outline of stages (1) to (4), where 31 is the membrane formation cell, g is a gaseous stream, and L is the liquid that the liquid membrane forms.

The stages are described below in relation with the apparatus of this invention.

(1) Liquid Immersion.

The membrane generation means 30 are partially immersed in the liquid supplying means 40. In FIGS. 1A, and 1B, such liquid supplying means comprise a liquid container 41 that contains liquid up to a determined liquid level 42.

As illustrated in FIG. 1B, by virtue of the rotation of the membrane generation means 30, the membrane generation means 30 are submerged in the liquid of container 41 in position A. The liquid completely floods the cells 31.

(2) Membrane Formation.

The disc rotates to position B, where membrane cells 31 that were submerged, now emerge, and the liquid spills over the container 41. However, by virtue of the surface tension of the liquid, aqueous membranes are generated in each cell 31 emerging from the liquid of container 41.

According to FIG. 3B, a pair of side membranes 311 are formed in side orifices 322 of cell 31. Besides, an upper membrane 312 is formed in the widest portion of the structure, and a lower membrane 313 in the thinnest portion of cell 31. In addition, and to a lesser extend, internal membranes that are not illustrated are formed, which are parallel to membranes 312 and 313 in the interior of the membrane cell 31. Someone or all of the referred membranes may be formed.

Once the membrane cells 31 emerge from the contained liquid located inside the container 41, the membranes 311, 312 and 313 are formed.

(3) Upcoming Air and Membrane Breakage.

The membrane cell 31 with a determined shape is submerged into an especial liquid. An aqueous membrane of the especial liquid is formed, and an airflow is applied to it, so that the membrane collapses and gets sprayed out into thousands of particles. The air suspended particles are trapped by the membrane spray, and are decanted.

The membrane cells 31 provide the system of the invention with channel, space, and time means for the already humidified particles that are still dispersed in the gas, to precipitate and agglutinate.

As shown in FIG. 1B, the induced air by fan 21 is set in contact with membrane cells 31 in the C position.

The air flow directly collide on the aqueous membranes 311, 312, and 313, which upon receiving the air flow, collapse, spraying themselves into thousands of small particles of the liquid that formed the membrane.

The air stream, in the first place, breaks the upper membrane 312, comes into the interior of the membrane cell 31, and breaks the side membranes 311 and the intermediate membrane, and finally the lower membrane 313, immediately entering into chamber 35.

The solid particles and pollutants accompanying the gaseous stream are decanted as a result of the saturation they underwent at the time of membrane breakage. This effect traps the suspended particles by changing their weight and precipitating them.

In order to effectively trap small particles, it is necessary for the particles to enter into contact with the membrane, and make it collapse. While the membrane collapses, the air comes into membrane cell 31, the membrane implodes, and the liquid film from which the membrane was made of, covers the particle. The smaller the portion of the collapsed membrane is, the smaller the particles that can be trapped. This system traps all of the detectable particles.

Optionally, the liquid from the membrane may contain a disinfectant, so the trapped particle in the membrane will subsequently be disinfected. The suspended particles can be impregnated with a bactericidal and aroma bio-absorption liquid, causing the killing of bacteria, viruses, and other harmful germs.

The liquid membranes described herein are collapsed upon contact with the small particles, such as dust, and the portions of the collapsed membrane are capable of humidifying one-micron-size particles. This way, particles in the air are collected and agglutinated.

Simultaneously, particles from the liquid of the collapsed membrane are transferred to the air stream, and humidify it. Aromatizers can be alternatively aggregated, besides they are transferred to the air stream, and aromatize it. The airflow resulting from the process comes out completely clean, and humidifies, and aromatizes the environment.

The liquid spray created by virtue of the membrane breakage favors the liquid transfer toward the gaseous stream.

The membrane cells 31 have an entry area bigger than the exit area, by virtue of such characteristic; the gaseous stream comes out with a higher speed than the speed it comes in.

By virtue of the shape of membrane cells 31, similar to an ejector, the air stream coming into membrane cells 31 in positions C, is accelerated and collides at a higher speed on the surface of the liquid contained inside chamber 35. The air collides on the liquid surface at an optimal angle, close to 45°, strikes with the liquid surface, and absorbs other liquid portion.

As can be seen in FIG. 1B, the air comes in only through cells C1 and C2. The later means the airflow can be controlled by calculating the cell dimensions and the rotational speed of the membrane generation means 30. Consequently, the composition of the escaping gas can be controlled.

Besides, the air is channeled in the cells at position C (FIG. 1B) so that a uniform flow that collides on the liquid surface inside the chamber 35 is obtained.

By virtue of the membrane generation rotating means, the following is achieved:

a) Removal of pollutant particles and dust;

b) Mass-transfer of liquid particles sprayed on the gas stream;

c) Mass-transfer of liquid particles due to the gas stream collision at an increased speed, and at an optimal angle, close to 45°, on the liquid surface.

(4) Humidified Air Ejection.

Once the gaseous stream strikes against the liquid surface, it absorbs a certain amount of liquid; the gas enriched with liquid particles is directed toward the exterior coming out through cells 31 in position D (FIG. 1B).

The cells 31 in position D are uncovered as previously formed membranes on stages A and B were collapsed in stage C. Thus the humidified air freely flows through them toward the exterior of the system.

The apparatus of this invention comprises also exterior channels 51 placed on the ejection means 50 to uniform the exiting humidified air stream.

The exterior channels 51 have walls providing a contact surface for the humidified air (enriched air), such surface aims to provide a surface for liquid condensation that over saturates the gaseous stream, so that the additional liquid condensates in such surface and slides toward the interior of the receptacle. This way, the exiting gas contains the proper amount of liquid.

In addition, the apparatus of this invention comprises electronic or non-electronic control means 60, to control the switching on and off of the unit, the liquid level in container 41, the fan speed 21, and the rotational speed of the membrane generation means 30, thus controlling the composition of the exiting gas.

By virtue of the different parts of the system and the apparatus of this invention, the vapor is absorbed in the gaseous stream in the following stages:

a) At the time following the liquid membrane breakage;

b) When the gaseous stream makes contact with the liquid surface inside the chamber 35;

c) Upon discharge of the enriched stream through the open cells; and d) Upon discharge of the enriched gaseous stream in the exterior channels.

The higher amount of vapor is transferred to the gaseous stream at the contact stage with the liquid surface inside the chamber 35.

As it will be readily apparent to a technician in the art, the gas and liquid streams used in the invention are of any kind depending on the application. For instance, if it is desired to provide a pesticide to an air stream, the liquid should consist of the chosen pesticide and the gas would be air. If it is desired to provide a combustible mixture, the liquid should be selected among any liquid hydrocarbons and the gas should be selected between hydrogen, and oxygen.

For humidifiers and aromatizers, the liquid consists of water with aromatizing chemical agents and for such applications it is preferred any liquid with bactericidal and bio-absorption soapy abilities.

The removal system for air suspended particles has an application in electronic appliances for home or office use, for air filtration systems, for decorative or publishing purposes in public areas, for humidifying greenhouses, for apparatus to pour fragrances or chemical agents in controlled amounts, air purifying systems of vehicles, airplanes, etc. And in purification systems of industries, hospitals.

For the purification of environmental air, it is possible to combine the system and the apparatus of this invention with removal methods for atmospheric air pollutants, for example, the method described in U.S. Pat. No. 5,227,144 where it is described a procedure for air purification by reaction with chemical products in liquid phase at different stages.

The liquid membrane generation means 30, in the preferred embodiment of the invention has been illustrated as a plurality of membrane cells 31 in a cylindrical arrangement. However, as it will be evident for a technician in the art, the arrangement may change. For example, a block of cells through which the air circulates can be placed with the proviso that the liquid supplying means floods or baths such block of cells. A block of cells for membrane generation is considered to be included within the scope of this invention.

The invention claimed is:

1. A system for mass transfer and elimination of contaminants, comprising:
  gas convection means for providing a gaseous stream;
  membrane generation means for generating a membrane cell;
  liquid supplying means for providing a liquid to the membrane generation means; and
  ejection means for providing an exit for the gaseous stream,
  wherein a liquid membrane is generated by said membrane cell when said membrane cell passes through said liquid supplying means, and
  wherein said liquid membrane collapses when in contact with the gaseous stream from said gas convection means, and
  wherein the collapsed liquid membrane removes contaminants from the gaseous stream while simultaneously transferring liquid molecules to the gaseous stream, and
  wherein said membrane generation means comprises a plurality of discs and a plurality of plates in a cylindrical arrangement to form a plurality of membrane cells.

2. A system according to claim 1, wherein the plurality of discs include a plurality of slots and a plurality of orifices.

3. A system according to claim 1, wherein an interior part of the cylindrical arrangement defines a chamber in which the contaminants from the gaseous stream are decanted.

4. A system according to claim 1, wherein one of the plurality of membrane cells that passes through the liquid supplying means forms one of a side liquid membrane in a side orifice of one of the plurality of membrane cells, an upper membrane in a widest portion of one of the plurality of membrane cells, a lower membrane in a thinnest portion of one of the plurality of membrane cells and a parallel internal membrane in an interior part of one of the plurality of membrane cells.

5. A system according to claim 1, wherein the liquid comprises water, and wherein the gaseous stream comprises air.

6. A device for mass transfer and elimination of contaminants, comprising:
  a housing;
  a fan for forcing a gaseous stream into an interior of said housing;
  a container for containing a liquid in said housing;
  a plurality of membrane cells disposed in a cylindrical arrangement and rotatably mounted within said housing,
  wherein a liquid membrane is generated when at least one of said plurality of membrane cell passes through the liquid, and
  wherein said liquid membrane collapses when in contact with the gaseous stream, and
  wherein the collapsed liquid membrane removes contaminants from the gaseous stream while simultaneously transferring liquid molecules to the gaseous stream, and
  wherein an interior part of the cylindrical arrangement defines a chamber in which the contaminants from the gaseous stream are decanted.

7. A device according to claim 6, wherein the liquid comprises water, and wherein the gaseous stream comprises air.

8. A device according to claim 6, further comprising aromatizers and disinfectants.

9. A device for mass transfer and elimination of contaminants, comprising:
  a housing;
  a fan for forcing a gaseous stream into an interior of said housing;
  a container for containing a liquid in said housing;
  a plurality of membrane cells disposed in a cylindrical arrangement and rotatably mounted within said housing,
  wherein a liquid membrane is generated when at least one of said plurality of membrane cell passes through the liquid, and
  wherein said liquid membrane collapses when in contact with the gaseous stream, and
  wherein the collapsed liquid membrane removes contaminants from the gaseous stream while simultaneously transferring liquid molecules to the gaseous stream, and
  wherein at least one membrane cell has an entry surface area larger than an exit surface area, thereby causing the gaseous stream to exit at a higher velocity than a velocity of the gaseous stream when entering said at least one membrane cell.

10. A device according to claim 6, further comprising exterior channels having walls to provide a contact surface for the gaseous stream as it exits from the housing.

11. A device for mass transfer and elimination of contaminants, comprising:
  a housing:
  a fan for forcing a gaseous stream into an interior of said housing;
  a container for containing a liquid in said housing;
  a plurality of membrane cells disposed in a cylindrical arrangement and rotatably mounted within said housing,
  wherein a liquid membrane is generated when at least one of said plurality of membrane cell passes through the liquid, and
  wherein said liquid membrane collapses when in contact with the gaseous stream, and
  wherein the collapsed liquid membrane removes contaminants from the gaseous stream while simultaneously transferring liquid molecules to the gaseous stream, and
  wherein at least one of said plurality of membrane cells comprises a plurality of discs and a plurality of plates.

12. A device according to claim 11, wherein the plurality of discs include a plurality of slots and a plurality of orifices.

13. A device for mass transfer and elimination of contaminants, comprising:
  a housing;
  a fan for forcing a gaseous stream into an interior of said housing;
  a container for containing a liquid in said housing:
  a plurality of membrane cells disposed in a cylindrical arrangement and rotatably mounted within said housing,
  wherein a liquid membrane is generated when at least one of said plurality of membrane cell passes through the liquid, and
  wherein said liquid membrane collapses when in contact with the gaseous stream, and
  wherein the collapsed liquid membrane removes contaminants from the gaseous stream while simultaneously transferring liquid molecules to the gaseous stream, and
  wherein one of the plurality of membrane cells that passes through the liquid forms one of a side liquid membrane in a side orifice of one of the plurality of membrane cells, an upper membrane in a widest portion of one of the plurality of membrane cells, a lower membrane in a thinnest portion of one of the plurality of membrane cells and a parallel internal membrane in an interior part of one of the plurality of membrane cells.

14. A method of eliminating contaminants by a device comprising, a housing, a fan for forcing a gaseous stream into an interior of said housing, a container for containing a liquid, a plurality of membrane cells disposed in a cylindrical arrangement and rotatably mounted within said housing, wherein at least one of said plurality of membrane cells comprises a plurality of discs and a plurality of plates, the method comprising the steps of:

immersing at least one of said plurality of membrane cells in the liquid;

forming a liquid membrane by at least one of said plurality of membrane cells when said at least one membrane cell passes through the liquid;

collapsing the liquid membrane by contacting the liquid membrane with the gaseous stream; and ejecting the gaseous stream from the housing, whereby the collapsed liquid membrane removes contaminants from the gaseous stream while simultaneously transferring liquid molecules to the gaseous stream.

* * * * *